(12) United States Patent
Schäfer et al.

(10) Patent No.: US 8,291,798 B2
(45) Date of Patent: Oct. 23, 2012

(54) METHOD AND DEVICE FOR PRODUCING SMALL, THIN SHEETS FROM AN ACTIVE-INGREDIENT FILM

(75) Inventors: Wolfgang Schäfer, Ledgewood, NJ (US); Ronald Hackbarth, Koblenz (DE); Detlev Neuland, West Caldwell, NJ (US)

(73) Assignee: LTS Lohmann Therapie-Systeme AG, Andernach (DE)

( * ) Notice: Subject to any disclaimer, the term of this patent is extended or adjusted under 35 U.S.C. 154(b) by 343 days.

(21) Appl. No.: 12/784,175

(22) Filed: May 20, 2010

(65) Prior Publication Data

US 2010/0224042 A1 Sep. 9, 2010

Related U.S. Application Data

(62) Division of application No. 10/467,894, filed as application No. PCT/EP02/01107 on Feb. 4, 2002, now Pat. No. 7,749,417.

(60) Provisional application No. 60/268,805, filed on Feb. 14, 2001.

(30) Foreign Application Priority Data

Mar. 5, 2001 (DE) .................. 101 10 494

(51) Int. Cl.
*B26D 7/06* (2006.01)
*B28B 11/16* (2006.01)
*B28B 11/12* (2006.01)

(52) U.S. Cl. ........... 83/86; 83/84; 83/90; 83/91; 83/151; 83/649; 83/408; 83/418; 83/436.5; 242/419; 242/419.1; 242/419.4; 264/146; 264/157; 424/409; 424/434; 424/435; 424/443; 270/52.09; 270/58.07; 270/58.23

(58) Field of Classification Search ........................ None
See application file for complete search history.

(56) References Cited

U.S. PATENT DOCUMENTS

| | | | |
|---|---|---|---|
| 2,942,643 A | 6/1960 | Pucci et al. |
| 3,046,823 A | 7/1962 | Cole |
| 3,379,390 A | 4/1968 | De Hertel Eastcott |
| 3,656,513 A | 4/1972 | Evans et al. |

(Continued)

FOREIGN PATENT DOCUMENTS

DE 949169 9/1956

(Continued)

*Primary Examiner* — Jeffrey Wollschlager
(74) *Attorney, Agent, or Firm* — Birch, Stewart, Kolasch & Birch, LLP

(57) ABSTRACT

The invention relates to a method and a device for producing small, thin sheets from an active-ingredient film (2), in which the latter is produced by casting the film material onto a substrate material or by coating a substrate material, storing it with or without substrate material on a reel, pulling it off the reel and cutting it. It achieves the object of designing a method of this type in such a way that with this method small sheets can be produced as exactly as possible in predetermined sizes. To do this, the active-ingredient film (2) is pulled off automatically, is separated from a substrate material which, if present, and in tensioned form, is fed to a cutting station and is cut, in the feed direction, into long, narrow strips (7) of predeterminable width, and the long strips (7) are brought together in the feed direction and together are fed by a further feed device (10) to a transverse cutter (11), which cuts through the combined long strips (7) at predetermined intervals.

27 Claims, 1 Drawing Sheet

U.S. PATENT DOCUMENTS

| | | |
|---|---|---|
| 4,008,351 A | 2/1977 | Inoue et al. |
| 4,197,289 A | 4/1980 | Sturzenegger et al. |
| 4,536,174 A | 8/1985 | Dreckmann |
| 5,311,801 A | 5/1994 | Uno |
| 5,816,030 A | 10/1998 | Carlberg et al. |
| 6,106,930 A | 8/2000 | Ludwig |
| 6,125,730 A | 10/2000 | Jacques |
| 6,216,842 B1 | 4/2001 | Beale et al. |
| 6,659,442 B1 | 12/2003 | Steinborn et al. |
| 7,114,422 B1 | 10/2006 | Neuland et al. |
| 7,370,563 B2 | 5/2008 | Neuland et al. |

FOREIGN PATENT DOCUMENTS

| | | |
|---|---|---|
| DE | 19925339 | 12/2000 |
| WO | WO-99/42397 | 8/1999 |

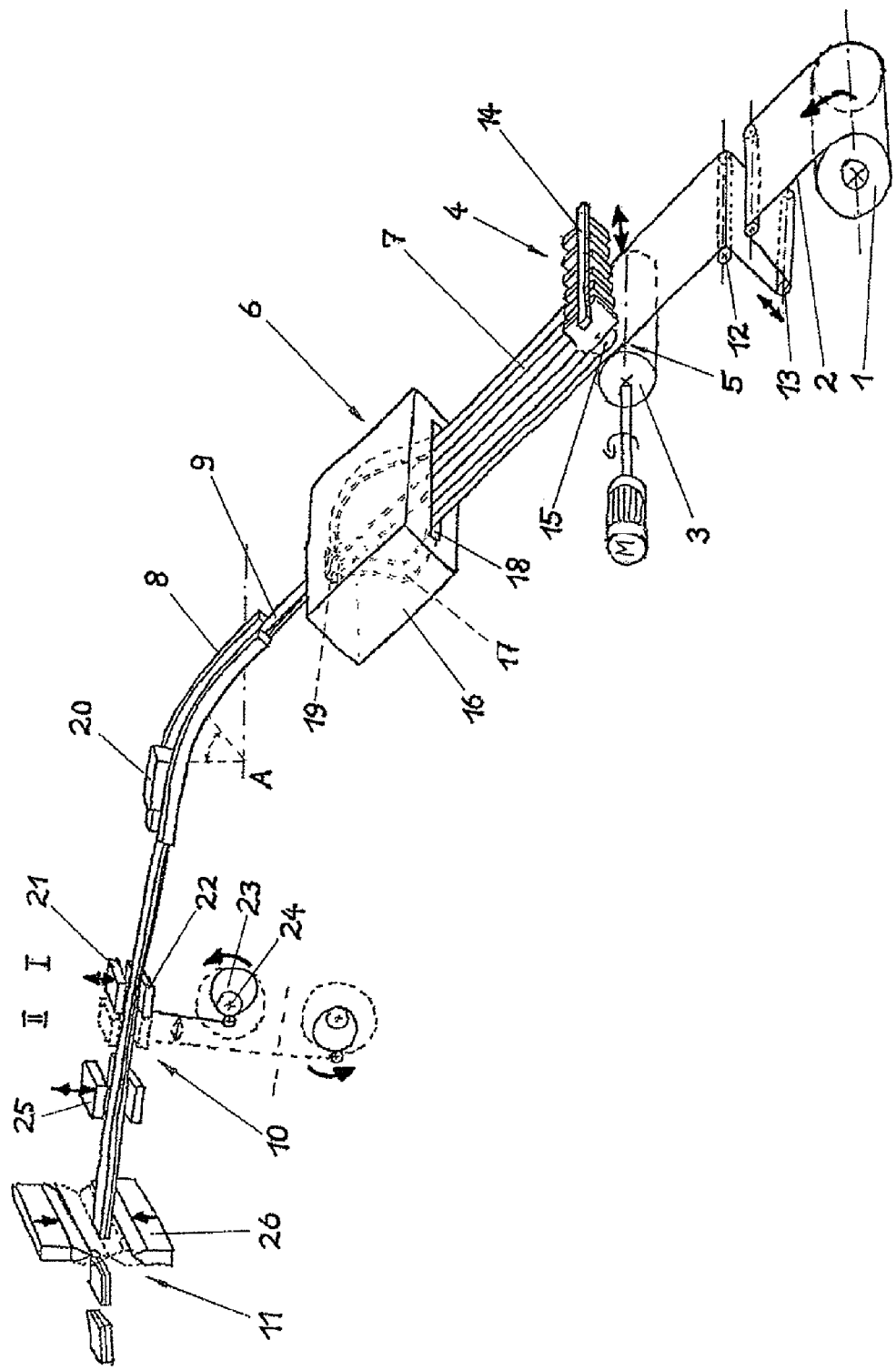

METHOD AND DEVICE FOR PRODUCING SMALL, THIN SHEETS FROM AN ACTIVE-INGREDIENT FILM

CROSS REFERENCE TO RELATED APPLICATIONS

This Application is a Divisional of application Ser. No. 10/467,894, filed on Aug. 13, 2003, now U.S. Pat. No. 7,749,417 which is a national phase of PCT International Application No. PCT/EP 02/01107, filed on Feb. 4, 2002, which claimed priority to German Application No. 101 10 494.4, filed Mar. 5, 2001, and U.S. Application No. 60/268,805, filed Feb. 14, 2001. All of which are hereby incorporated by reference in their entireties.

BACKGROUND OF THE INVENTION

1. Field of the Invention

The invention relates to a method and a device for producing small, thin sheet film of one or more active ingredients, in particular for use as a metering and administration form for medicaments.

2. Description of the Related Art

In addition to the known metering forms for medicaments, such as tablets, capsules, droplets or similar administration forms, there is also the "wafer" form of administration. This is a small, thin sheet comprising or containing an active-ingredient film with a predetermined quantity of active ingredient, the thickness and dimensions of which are adapted to the quantity of active ingredient which is to be dispensed. Since the contact area of the wafer is directly related to the metered quantity of the active ingredient, its dimensions must as far as possible correspond to the calculated dimensions and lie within the tolerance range. Therefore, the wafer is complex to produce.

It is known to produce the active-ingredient film by means of casting methods or by a coating method. Usually, the active-ingredient film is cast onto or applied to the film material in some other way, with or without the substrate material, is wound up into reels and is stored. If the active-ingredient film is wound up together with the substrate material, during the subsequent processing of the active-ingredient film to form small, thin sheets, the substrate material is separated from the active-ingredient film and is wound up separately. The thin, flexible active-ingredient film is cut. The actual dimensions produced frequently fail to correspond to the required dimensional tolerances which have been set down in accordance with the metering of the medicament, which is reflected in the active-ingredient tolerance over the area.

SUMMARY OF THE INVENTION

It is an object of the invention to provide a method for producing small, thin sheets from an active-ingredient film that makes it possible to produce small sheets as precisely as possible in predetermined sizes.

In a method, small, thin sheets from an active-ingredient film are produced. A device for carrying out the method is also specified.

BRIEF DESCRIPTION OF THE DRAWINGS

FIG. 1 shows a device for producing small, thin sheets from an active-ingredient film.

DETAILED DESCRIPTION

Accordingly, in a method which is used to produce small, thin sheets from an active-ingredient film, after this film has been produced by casting the film material onto a substrate material or coating a substrate material and has been stored on a reel with or without substrate material, and in which the active-ingredient film is pulled off the storage reel and cut, the active-ingredient film is automatically pulled off the storage reel, is separated from a substrate material which, if present, and is fed in tensioned form to a strip-cutting station, where it is initially cut into narrow strips of predetermined width in the longitudinal direction, which corresponds to the feed direction. Then, the strips are brought together in the feed direction and are fed as a group, by a further feed device, to a transverse cutter, which cuts through the group at predetermined intervals. The longitudinal and transverse cutting of the active-ingredient film, which operations follow one another physically and in terms of time, produces quadrilateral, in particular rectangular or square, small sheets, the active-ingredient film, at least in terms of its width, being dimensioned in such a way that it is cut into small sheets of predetermined size without any remainder or waste. The size of the small sheets influences the metering. The fact that the active-ingredient film is fed to the strip-cutting station under a prestress facilitates the cutting operation. The fact that the film strips which have been cut in the longitudinal direction are also brought together to form a group of strips likewise facilitates and simplifies the transverse cutting and, moreover, increases the process reliability and dimensional accuracy when producing the small sheets.

Advantageously, the operations of pulling the active-ingredient film of the storage reel and feeding it to the longitudinal cutting station take place continuously, as does the longitudinal cutting into film strips.

To facilitate the longitudinal cutting, a prestress is produced in the active-ingredient film, leading to this film being smoothed and therefore to a precise longitudinal cutting operation. To do this, the active-ingredient film can simply be subjected to a load transversely to the feed direction, in particular by means of a defined weight which, in combination with the width of the active-ingredient film, determines the prestressing.

The cut film strips are preferably brought together to form a stack, so that they rest smoothly on top of one another. The further feeding of the film strips in a simple manner takes place intermittently and can be of reliable design. In order to be fed and pushed towards the transverse cutter, the stack is gripped and clamped by clamping jaws which engage on its upper and lower sides is intermittently pushed to the transverse cutter. To enable this method step also to be carried out with a high process reliability and dimensional accuracy, the stack, upstream of the clamping device, in order to ensure that the strips are arranged precisely on top of one another, in combination with further smoothing and producing a prestress, is guided in a sliding manner so that it maintains its dimensions, in the process being pulled by the feed device and fed to the transverse cutter, relative movements between the individual strips and different lengthening of the material or strips being suppressed.

A device for carrying out the method as a holding device for a storage reel with the film material, a feed roller which is driven by electric motor for pulling the active-ingredient film off the storage reel at least in its width, a strip-cutting device, formed by the feed roller and a cutting-blade device which interacts therewith, a device for bringing together and stacking the said cut film strips (stacking device) and a further feed device therefor and a transverse cutting device. Means for smoothing the stack of strips and, in conjunction with the further feed device, means for producing a prestress are arranged between the stacking device and the further feed device.

Two guide rollers for the active-ingredient film, between which a dancer roll rests on the active-ingredient film in order to produce a stress in the latter, are arranged in the feed region between the storage reel and the feed roller, parallel to these components. The cutting-blade device has round cutting discs which can rotate next to and at a distance from one another, are held parallel to the feed direction next to and at a distance from one another on a holding device and are pressed onto the active-ingredient film which is advanced on the feed roller. The distance between the cutting discs is adjustable.

A combining and stacking device for the cut fed strips forms part of the overall device. A device of this type is described in DE 199 25 339 A1.

The film strips which are to be brought together and stacked are fed intermittently by means of a gripper feed system, which intermittently grips the stack and exerts a tensile force on it and which also pushes the stack to the transverse cutter.

A U-shaped three-sided slideway, in which the stack is moved by the gripper feed system, is arranged between the stacking device and the gripper feed system. Weights which are held in a stationary position but so that they can move in vertical guides and rest on the moving stack, thus smoothing the latter during its feed movement, are arranged on this slideway. The slideway is bent convexly about an axis which lies transversely with respect to the feed direction, as seen in plan view of the stack, so that a defined prestress is produced in the stack, which has to be overcome by the gripper feed system as a precisely defined resistance. The feed section of the gripper feed system determines the length of the small sheets.

The gripper feed system is provided with two clamping jaws, which are coupled to a drive by means of a conveyor cam and, with respect to the feed direction, are moved backward and forward, the clamping jaws, for the purpose of the forward movement, clamping the stack between them at a distance from that end of the stack is on the side of the transverse cutter and pull it off the slideway, counter to the resistance produced on the slideway, at the same time pushing the stack section of defined length which is situated in front of the gripper feed system, as seen in the feed direction, into the transverse cutter. The conveyor cam is eccentrically mounted, and the clamping jaws are in continuous engagement therewith, so that continuous rotation of the conveyor cam is converted into a defined forward and backward translational movement of the clamping jaws. A change in the dimensions or the shape of the conveyor leads to a change in the magnitude of the translational movement and therefore in the feed, with the result that the cut length of the stack and therefore the length of the small sheets can be predetermined.

The invention is explained below with reference to an exemplary embodiment. The associated drawing shows a device for producing small, thin sheets from an active-ingredient film, partially diagrammatically.

The device has a storage area 1 with a stock of active-ingredient film 2 of a thickness of approximately 0.05 mm, in a holding means which is not shown, a motor-driven (M) vacuum roller 3 and a feed roller for pulling the active-ingredient film 2 off the storage reel 1, a longitudinal cutting device 5, which is formed with the vacuum roller 3 and a cutting-blade device 4 which interacts with the latter, a stacking device 6 for the cut long strips 7, a three-sided slideway 8, which is U-shaped in cross section, for the stack 9 which is formed from the long strips 7, a gripper feed system 10 and a transverse cutting device 11 for the stack 9. Two guide rollers 12 for the active-ingredient film 2 are arranged between the storage reel 1 and the longitudinal cutting device 5, parallel to the storage reel 1, and a dancer roller 13, which acts on this active-ingredient film 2 for tautening this film, is arranged between these guide rollers 12.

The cutting-blade device 4 comprises a holding device 14, which is not shown in more detail, and rotatable round cutting disks 15, which are held next to one another on the holding device at an adjustable distance from one another, are oriented parallel to the feed direction of the active-ingredient film 2, are pressed onto the active-ingredient film 2 and cut the latter in the longitudinal direction, in accordance with their arrangement, as it is advanced by the vacuum roller 3. In the exemplary embodiment, the distance between the cutting disks 15 is 20 mm.

In a stacking block 16, the stacking device 6 has, for each long strip 7, a vacuum conveyor channel 17 which is coupled to a vacuum device (not shown) and, together with the other vacuum conveyor channels 17, arranged next to one another, is connected to a common entry 18. In the stacking block 16, the channels 17 run in such a way that they are brought together above one another at a common exit 19.

The stacking device 6 is followed by the three-sided slideway 8, which is bent around an axis A, which is arranged transversely to the feed direction or parallel to the axis of the vacuum roller 3 of the rollers 1, 12 and 13, and receives the stack 9 so as to guide its sides, the width between the side walls of the three-sided slideway 8 substantially corresponding to the width of the stack 9. In a vertical guide, which is not shown, a weight 20 of 120 g from the stack 9, resting on the stack and thus compressing and smoothing the latter.

As seen in the feed direction, the gripper feed system 10 is arranged downstream of the three-sided slideway 8, which gripper feed system has two clamping jaws 21 and 22, which are arranged one above the other, for intermittently gripping the stack 9 and are coupled to a drive 4 by means of an exchangeable, eccentric conveyor cam 23. These components (23, 24) move the clamping jaws 21, 22 forward and backward, with respect to the feed direction, during which movement the clamping jaws 21 and 22 pick up the stack 9 in their rear dead center position I and release it again at their front dead center position II.

The gripper feed system 10 is followed by guide jaws 25, between which the stack 9 slides toward the transverse cutting device 11, in which it is cut transversely between two cutting blades 26. The predeterminable length of the stack section is 25 mm, resulting in a wafer size of 20×25 mm.

The wafers which have been produced are then packaged in dispensers, blister packs or tubular bags on a packaging machine.

The invention claimed is:

1. An apparatus for producing small, thin sheets from an active-ingredient film, the apparatus comprising:
    a reel configured to hold the film;
    a first feeding device positioned downstream from the reel to pull the film off the reel in a feeding direction;
    a first cutting device positioned downstream from the first feeding device, the first feeding device feeding the film to the first cutting device, the first cutting device being arranged to cut the film into long, narrow strips of predeterminable width;
    a stacking device positioned downstream from the first cutting device to receive the long strips from the first cutting device, the stacking device being configured to arrange the long strips on top of one another in the form of a stack of individual strips;

a second feeding device positioned downstream from the first cutting device to feed the stack of individual strips through a slideway to a second cutting device to cut through the stack of individual strips at predetermined intervals, the slideway having two side walls and a bottom wall to provide a U-shaped cross-section, the slideway being bent convexly around an axis which lies transversely to the feeding direction to produce a prestress in the stack of individual strips to smooth the strips, and the width between the two side walls substantially corresponds to the width of the stack of individual strips, wherein the second feeding device includes a pair of guide jaws arranged between the slideway and the second cutting device such that the stack of individual strips slides between the pair of guide jaws, one guide jaw of the pair of guide jaws being arranged above the stack of individual strips, and the other guide jaw of the pair of guide jaws being arranged below the stack of individual strips.

2. The apparatus according to claim 1, wherein the first feeding device includes a vacuum roller driven by a motor, the vacuum roller contacting the film as it is fed from the reel.

3. The apparatus according to claim 1, further comprising:
two guide rollers arranged between the reel and the first cutting device, the two guide rollers being arranged parallel to the reel and in contact with the film; and
a dance roller, the dancer roller being located between the two guide rollers and acting on the film located between the two guide rollers to provide tension to the film.

4. The apparatus according to claim 1, wherein the first cutting device includes a cutting blade device having a holding device supporting a plurality of round cutting discs, the round cutting discs being adjustably spaced, and the round cutting discs being oriented parallel to the feeding direction.

5. The apparatus according to claim 1, wherein the stacking device includes a plurality of vacuum conveyor channels, the entry of each channel being arranged in a substantially horizontal plane, and the exit of each channel being arranged in a substantially vertical plane, with one channel being provided for each of said long strips.

6. The apparatus according to claim 1, further comprising at least one weight being provided in a vertical guide at a stationary position on the slideway, the weight being movable in the vertical guide and configured to rest on the stack of individual strips, the width of the weight being substantially the same as the width between the two side walls.

7. The apparatus according to claim 1, further comprising a gripper feed system located between the slideway and the pair of guide jaws, the gripper feed system being configured to intermittently grip the stack of individual strips and feed the stack to the second cutting device.

8. An apparatus for producing small, thin sheets from an active-ingredient film, the apparatus comprising:
a reel configured to hold the film;
a first feeding device positioned downstream from the reel to pull the film off the reel in a feeding direction;
a first cutting device positioned downstream from the first feeding device, the first feeding device feeding the film to the first cutting device, the first cutting device being arranged to cut the film into long, narrow strips of predeterminable width;
a stacking device positioned downstream from the first cutting device to receive the long strips from the first cutting device, the stacking device being configured to arrange the long strips on top of one another in the form of a stack of individual strips;
a second feeding device positioned downstream from the first cutting device to feed the stack of individual strips through a slideway to a second cutting device to cut through the stack of individual strips at predetermined intervals; and
at least one weight being provided in a vertical guide at a stationary position on the slideway, the weight being movable in the vertical guide and configured to rest on the stack of individual strips to prestress and smooth the stack while the stack of individual strips are fed through the slideway, wherein the second feeding device includes a pair of guide jaws arranged between the slideway and the second cutting device such that the stack of individual strips slides between the pair of guide jaws, one guide jaw of the pair of guide jaws being arranged above the stack of individual strips, and the other guide jaw of the pair of guide jaws being arranged below the stack of individual strips.

9. The apparatus according to claim 8, wherein the first feeding device includes a vacuum roller driven by a motor, the vacuum roller contacting the film as it is fed from the reel.

10. The apparatus according to claim 8, further comprising:
two guide rollers arranged between the reel and the first cutting device, the two guide rollers being arranged parallel to the reel and in contact with the film; and
a dance roller, the dancer roller being located between the two guide rollers and acting on the film located between the two guide rollers to provide tension to the film.

11. The apparatus according to claim 8, wherein the first cutting device includes a cutting blade device having a holding device supporting a plurality of round cutting discs, the round cutting discs being adjustably spaced, and the round cutting discs being oriented parallel to the feeding direction.

12. The apparatus according to claim 8, wherein the stacking device includes a plurality of vacuum conveyor channels, the entry of each channel being arranged in a substantially horizontal plane, and the exit of each channel being arranged in a substantially vertical plane, with one channel being provided for each of said long strips.

13. The apparatus according to claim 8, further comprising a gripper feed system located between the slideway and the pair of guide jaws, the gripper feed system being configured to intermittently grip the stack of individual strips and feed the stack to the second cutting device.

14. An apparatus for producing small, thin sheets from an active-ingredient film, the apparatus comprising:
a reel configured to hold the film;
a first feeding device positioned downstream from the reel to pull the film off the reel in a feeding direction;
a first cutting device positioned downstream from the first feeding device, the first feeding device feeding the film to the first cutting device, the first cutting device being arranged to cut the film into long, narrow strips of predeterminable width;
a stacking device positioned downstream from the first cutting device to receive the long strips from the first cutting device, the stacking device being configured to arrange the long strips on top of one another in the form of a stack of individual strips;
a second feeding device positioned downstream from the first cutting device to feed the stack of individual strips through a slideway to a second cutting device to cut through the stack of individual strips at predetermined intervals, the slideway having two side walls and a bottom wall to provide a U-shaped cross-section, the slideway being bent convexly around an axis which lies transversely to the feeding direction to produce a prestress in the stack of individual strips, and the width between the two side walls substantially corresponds to the width of the stack of individual strips, wherein the second feeding device includes a gripper feed system configured to intermittently grip the stack of individual strips after receiving the stack of individual strips from the slideway, the gripper feed system including two clamping jaws that are coupled to a drive by an eccentric conveyor cam that moves the clamping jaws backward and forward with respect to the feeding direction, the clamping jaws clamp the stack of individual strips securely during forward movement.

15. The apparatus according to claim 14, wherein the first feeding device includes a vacuum roller driven by a motor, the vacuum roller contacting the film as it is fed from the reel.

16. The apparatus according to claim 14, further comprising:

two guide rollers arranged between the reel and the first cutting device, the two guide rollers being arranged parallel to the reel and in contact with the film; and a dance roller, the dancer roller being located between the two guide rollers and acting on the film located between the two guide rollers to provide tension to the film.

17. The apparatus according to claim 14, wherein the first cutting device includes a cutting blade device having a holding device supporting a plurality of round cutting discs, the round cutting discs being adjustably spaced, and the round cutting discs being oriented parallel to the feeding direction.

18. The apparatus according to claim 14, wherein the stacking device includes a plurality of vacuum conveyor channels, the entry of each channel being arranged in a substantially horizontal plane, and the exit of each channel being arranged in a substantially vertical plane, with one channel being provided for each of said long strips.

19. The apparatus according to claim 14, wherein the eccentric conveyor cam is an exchangeable eccentric conveyor cam.

20. The apparatus according to claim 14, further comprising at least one weight being provided in a vertical guide at a stationary position on the slideway, the weight being movable in the vertical guide and configured to rest on the stack of individual strips, the width of the weight being substantially the same as the width between the two side walls.

21. An apparatus for producing small, thin sheets from an active-ingredient film, the apparatus comprising:

a reel configured to hold the film;

a first feeding device positioned downstream from the reel to pull the film off the reel in a feeding direction;

a first cutting device positioned downstream from the first feeding device, the first feeding device feeding the film to the first cutting device, the first cutting device being arranged to cut the film into long, narrow strips of predeterminable width;

a stacking device positioned downstream from the first cutting device to receive the long strips from the first cutting device, the stacking device being configured to arrange the long strips on top of one another in the form of a stack of individual strips;

a second feeding device positioned downstream from the first cutting device to feed the stack of individual strips through a slideway to a second cutting device to cut through the stack of individual strips at predetermined intervals; and at least one weight being provided in a vertical guide at a stationary position on the slideway, the weight being movable in the vertical guide and configured to rest on the stack of individual strips to prestress and smooth the stack while the stack of individual strips are fed through the slideway, wherein the second feeding device includes a gripper feed system configured to intermittently grip the stack of individual strips after receiving the stack of individual strips from the slideway, the gripper feed system including two clamping jaws that are coupled to a drive by an eccentric conveyor cam that moves the clamping jaws backward and forward with respect to the feeding direction, the clamping jaws clamp the stack of individual strips securely during forward movement.

22. The apparatus according to claim 21, wherein the first feeding device includes a vacuum roller driven by a motor, the vacuum roller contacting the film as it is fed from the reel.

23. The apparatus according to claim 21, further comprising:

two guide rollers arranged between the reel and the first cutting device, the two guide rollers being arranged parallel to the reel and in contact with the film; and a dance roller, the dancer roller being located between the two guide rollers and acting on the film located between the two guide rollers to provide tension to the film.

24. The apparatus according to claim 21, wherein the first cutting device includes a cutting blade device having a holding device supporting a plurality of round cutting discs, the round cutting discs being adjustably spaced, and the round cutting discs being oriented parallel to the feeding direction.

25. The apparatus according to claim 21, wherein the stacking device includes a plurality of vacuum conveyor channels, the entry of each channel being arranged in a substantially horizontal plane, and the exit of each channel being arranged in a substantially vertical plane, with one channel being provided for each of said long strips.

26. The apparatus according to claim 21, wherein the eccentric conveyor cam is an exchangeable eccentric conveyor cam.

27. The apparatus according to claim 21, wherein guide elements are arranged between the gripper feed system and the second cutting device.

* * * * *